(12) United States Patent
Smith et al.

(10) Patent No.: US 12,202,645 B2
(45) Date of Patent: Jan. 21, 2025

(54) DISPLAY CONTAINER FOR DISPLAYING A BOTANICAL SPECIMEN

(71) Applicant: ALL PLASTIC, INC., Rancho Cordova, CA (US)

(72) Inventors: William Thomas Smith, Fair Oaks, CA (US); Cheryl Ann Smith, Fair Oaks, CA (US)

(73) Assignee: ALL PLASTIC, INC., Rancho Cordova, CA (US)

( * ) Notice: Subject to any disclaimer, the term of this patent is extended or adjusted under 35 U.S.C. 154(b) by 0 days.

(21) Appl. No.: 18/502,643

(22) Filed: Nov. 6, 2023

(65) Prior Publication Data

US 2024/0067404 A1   Feb. 29, 2024

Related U.S. Application Data

(63) Continuation of application No. 17/989,464, filed on Nov. 17, 2022, now Pat. No. 11,905,069, which is a continuation of application No. 17/552,992, filed on Dec. 16, 2021, now Pat. No. 11,655,074, which is a continuation of application No. 16/874,394, filed on May 14, 2020, now Pat. No. 11,235,909, which is a continuation-in-part of application No. 29/691,120, filed on May 14, 2019, now Pat. No. Des. 945,877.

(Continued)

(51) Int. Cl.
| | |
|---|---|
| *B65D 25/38* | (2006.01) |
| *A01G 9/14* | (2006.01) |
| *A47F 7/28* | (2006.01) |
| *A61L 9/12* | (2006.01) |
| *B65D 25/10* | (2006.01) |
| *B65D 25/54* | (2006.01) |
| *B65D 85/50* | (2006.01) |

(52) U.S. Cl.
CPC ............... *B65D 25/38* (2013.01); *A01G 9/14* (2013.01); *A47F 7/286* (2013.01); *A61L 9/12* (2013.01); *B65D 25/106* (2013.01); *B65D 25/54* (2013.01); *B65D 85/50* (2013.01); *B65D 2201/00* (2013.01)

(58) Field of Classification Search
CPC .. A01G 9/14; A47F 7/286; A61L 9/12; B65D 25/10; B65D 25/106; B65D 25/38; B65D 25/54; B65D 81/18; B65D 85/50; B65D 2201/00
USPC .......................... 206/423, 769–774, 775–783
See application file for complete search history.

(56) References Cited

U.S. PATENT DOCUMENTS

| | | | | |
|---|---|---|---|---|
| 1,998,681 | A | * | 4/1935 | Littleford, Jr. .......... F25D 3/125 62/457.1 |
| 2,765,194 | A |   | 10/1956 | Will |

(Continued)

FOREIGN PATENT DOCUMENTS

| | | | | |
|---|---|---|---|---|
| JP | 10324372 | A | * | 12/1998 |
| JP | 11215932 | A | * | 8/1999 |

(Continued)

*Primary Examiner* — Bryon P Gehman

(57) ABSTRACT

A display container for displaying an aromatic botanical specimen includes: (a) a container body for enclosing the botanical specimen and scented air having a scent of the botanical specimen; (b) at least one scent discharge port in the container body; and (c) an air pump coupled to the container body and operable to discharge the scented air from within the container body to the environment through the scent discharge port.

20 Claims, 9 Drawing Sheets

Related U.S. Application Data

(60) Provisional application No. 62/847,539, filed on May 14, 2019.

(56) References Cited

U.S. PATENT DOCUMENTS

| | | |
|---|---|---|
| 4,858,831 A | 8/1989 | Spector |
| D322,938 S | 1/1992 | Baroi |
| 5,355,718 A | 10/1994 | Mookherjee et al. |
| 5,369,978 A | 12/1994 | Mookherjee et al. |
| 5,782,358 A | 7/1998 | Walker |
| D412,646 S | 8/1999 | Credle, Jr. |
| D431,190 S | 9/2000 | Adachi et al. |
| D447,944 S | 9/2001 | Justice |
| D455,073 S | 4/2002 | Mizrahi |
| D463,979 S | 10/2002 | Rustioni |
| D468,636 S | 1/2003 | Weinstein et al. |
| D479,461 S | 9/2003 | Raymond et al. |
| D494,476 S | 8/2004 | Cwynar-Laska et al. |
| D498,502 S | 11/2004 | Duke |
| D531,514 S | 11/2006 | Harris |
| D550,967 S | 9/2007 | Huang |
| D555,983 S | 11/2007 | Tucker et al. |
| D572,086 S | 7/2008 | Matsumoto et al. |
| 7,644,536 B2 | 1/2010 | Farhadi |
| D616,044 S | 5/2010 | Tervo |
| D624,704 S | 9/2010 | Baker et al. |
| D635,031 S | 3/2011 | Themann |
| 8,393,485 B2 | 3/2013 | Gold et al. |
| D741,058 S | 10/2015 | Wiederman |
| D761,008 S | 7/2016 | Lande |
| 9,630,747 B2 | 4/2017 | Smith et al. |
| D800,845 S | 10/2017 | Sprague |
| 10,363,334 B2 | 7/2019 | Kuijper |
| 10,384,834 B2 | 8/2019 | Smith et al. |
| D892,231 S | 8/2020 | Jung et al. |
| D926,465 S | 8/2021 | Schaepers et al. |
| 2002/0157308 A1 | 10/2002 | Hanis |
| 2009/0261100 A1 | 10/2009 | Mcminn |
| 2012/0279992 A1 | 11/2012 | Wilder |
| 2013/0119059 A1 | 5/2013 | Toh et al. |
| 2016/0031605 A1 | 2/2016 | Bean et al. |
| 2016/0084563 A1* | 3/2016 | Ghiraldi ................ B65D 81/18 62/457.2 |
| 2020/0361661 A1 | 11/2020 | Smith et al. |

FOREIGN PATENT DOCUMENTS

| | | |
|---|---|---|
| JP | 2005000065 A | 1/2005 |
| JP | 2019022454 A | 2/2019 |
| WO | 2017204590 A1 | 11/2017 |
| WO | 2018217490 A1 | 11/2018 |

* cited by examiner

DISPLAY CONTAINER FOR DISPLAYING A BOTANICAL SPECIMEN

CROSS-REFERENCE TO RELATED APPLICATIONS

This application is a continuation of U.S. Non-Provisional application Ser. No. 17/989,464, filed on Nov. 17, 2022, which is a continuation of U.S. Non-Provisional application Ser. No. 17/552,992, filed on Dec. 16, 2021, now U.S. Pat. No. 11,655,074, which is a continuation of U.S. Non-Provisional application Ser. No. 16/874,394, filed on May 14, 2020, now U.S. Pat. No. 11,235,909, which claims the benefit of U.S. Provisional Application No. 62/847,539, filed on May 14, 2019, and which is a continuation-in-part of U.S. Design Application No. 29/691,120, filed on May 14, 2019, now U.S. Design Pat. No. D945,877, each of which is hereby incorporated herein by reference in its entirety.

FIELD

The specification relates generally to display containers, and more specifically, to display containers for displaying aromatic botanical specimens.

BACKGROUND

U.S. Pat. No. 9,630,747 B2 (Smith et al.) discloses a container for displaying, visualizing, and aroma sampling botanical materials—such as tea, cannabis, and the like including a container body, lid, and lens. The container body is shaped to define a mounting projection wherein a sample, such as a botanical sample, may be held. Container body and lid form an airtight seal. A sample may be visualized through the lens. In a preferred embodiment, lid is shaped to define scent openings permitting aroma sampling of a sample contained within. In one embodiment option, one or more projections secure a card bearing sample identification information.

U.S. Pat. No. 9,334,086 B2 (Bean et al.) discloses a locking sample case used for displaying high-valued aromatic materials. The sample case has a stage for holding the material, a cover configured to mate with the stage, and a base to mate with the mated stage and cover assembly. The base has a lock mechanism to lock the stage to the base. The cover has tabs that secure the cover to the stage. The sample case is configured so that when the stage is mated to the base, the tabs cannot disengage from the base, so the cover cannot be removed from the stage when the stage is mated with the base. The cover has windows and closable vents to allow a potential buyer to see and smell the aromatic material. The sample case is configured to have a tether that can only be detached when the base is decoupled from the stage.

SUMMARY

The following summary is intended to introduce the reader to various aspects of the applicant's teaching, but not to define any invention.

According to some aspects, a display container for displaying an aromatic botanical specimen includes: (a) a container body for enclosing the botanical specimen and scented air having a scent of the botanical specimen, at least a portion of the container body generally transparent to facilitate viewing of the botanical specimen; (b) at least one scent discharge port in the container body; and (c) an air pump coupled to the container body. The air pump cooperates with the container body to define an interior volume of the display container. The air pump is movable between an expanded state and a contracted state, and movement of the air pump toward the contracted state reduces the interior volume for discharging the scented air from within the container body to the environment through the scent discharge port.

In some examples, movement of the air pump toward the expanded state increases the interior volume for drawing air into the interior volume from the environment through the scent discharge port.

In some examples, the interior volume comprises an air chamber of the air pump, and movement of the air pump to the contracted state collapses the air chamber. In some examples, movement of the air pump to the expanded state expands the air chamber.

In some examples, the air pump comprises a resiliently deformable bulb mounted to the container body, the bulb having a bulb interior defining the air chamber. In some examples, when the air pump is in the expanded state, the bulb projects outwardly from an exterior surface of the container body and is depressible inwardly toward the container body to move the air pump toward the contracted state and collapse the air chamber. In some examples, when depressed, the bulb is urged outwardly away from the container body to move the air pump toward the expanded state and expand the air chamber.

In some examples, the interior volume comprises an interior space in the container body for containing the botanical specimen and the scented air.

The interior space is bounded by a container base for supporting the container in an upright position, a container top wall opposite the base, and a container sidewall extending between the container base and the container top wall.

In some examples, the scent discharge port is in the container top wall and the air pump is mounted to the container sidewall.

In some examples, the container top wall and the container sidewall are generally transparent to facilitate viewing of the botanical specimen.

In some examples, the container includes a platform in the container body, the platform separating the interior space into an upper compartment for holding the botanical specimen and a lower compartment for holding a humidity control package.

In some examples, the container includes a specimen retainer in the container body for retaining the botanical specimen at a predetermined location. In some examples, the specimen retainer comprises a mounting spike for impaling the botanical specimen.

In some examples, the container body includes a viewing lens for viewing the botanical specimen.

According to some aspects, a display container for displaying an aromatic botanical specimen includes: (a) a container body for enclosing the botanical specimen and scented air having a scent of the botanical specimen; (b) at least one scent discharge port in the container body; and (c) an air pump coupled to the container body and spaced apart from the scent discharge port. The air pump is operable to discharge the scented air from within the container body to the environment through the scent discharge port.

According to some aspects, a method of sampling an aroma of a botanical specimen displayed in a display container includes contracting an air pump coupled to the display container to discharge scented air having a scent of the botanical specimen from within the container to environment through at least one scent discharge port in the container.

In some examples, contracting the air pump comprises reducing an interior volume of the display container. In some examples, the interior volume comprises an air chamber of the air pump, and contracting the air pump comprises collapsing the air chamber. In some examples, the air pump comprises a resiliently deformable bulb having a bulb interior defining the air chamber, and contracting the air pump comprises depressing the bulb to collapse the air chamber.

In some examples, the method further includes expanding the air pump to draw air into the display container from the environment, and after the expanding step, repeating the contracting step. In some examples, expanding the air pump comprises increasing an interior volume of the display container. In some examples, the interior volume comprises an air chamber of the air pump, and expanding the air pump comprises expanding the air chamber. In some examples, the air pump comprises a resiliently deformable bulb having a bulb interior defining the air chamber, and expanding the air pump comprises releasing the bulb to expand the air chamber.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors, or owners do not intend to abandon, disclaim, or dedicate to the public any such invention by its disclosure in this document.

In retail or other environments, product specimens can be displayed in secure display containers to allow for viewing of the product specimens while deterring theft or misplacement. In some cases, it may be desirable to sample an aroma of the product specimen, for example, if the aroma may be a consideration in the selection and/or purchase of the product. In such cases, it may be advantageous to allow for the aroma of the product specimen to be sampled while the product specimen remains in the display container.

The present application discloses aspects of display containers that can facilitate aroma sampling of product specimens held in the display containers. The product specimens can include, for example, aromatic botanical specimens such as, for example, a Cannabis flower (commonly referred to as a "bud").

Figure 1:
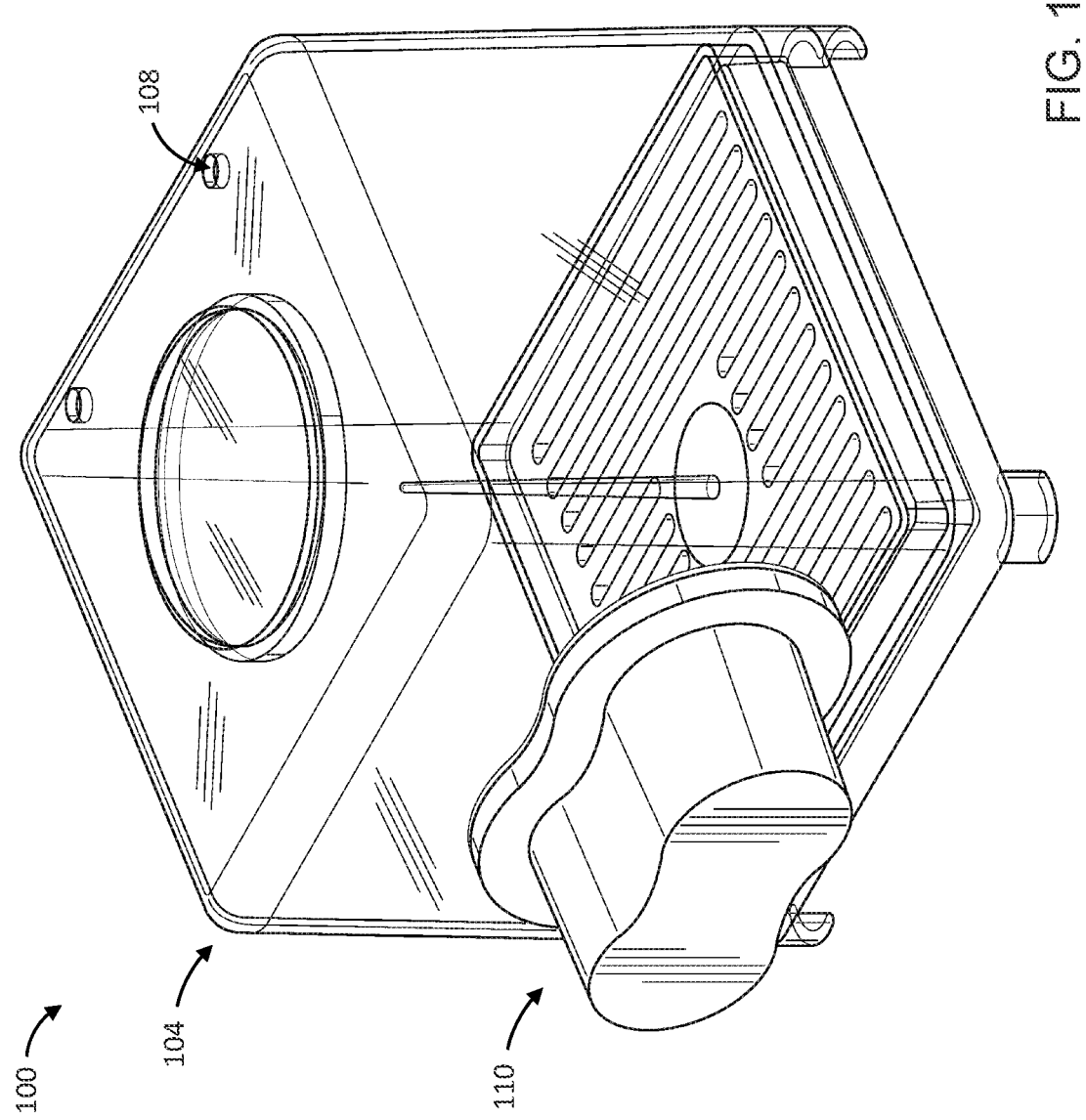
FIG. 1 is a perspective view of an example display container.

Referring to FIG. 1, an example display container 100 for displaying an aromatic botanical specimen 102 (shown schematically in FIG. 5 as a cannabis flower) is illustrated. The container 100 includes a container body 104 for enclosing the botanical specimen 102 and scented air 106 (FIG. 5) having a scent of the botanical specimen 102. In the example illustrated, at least a portion of the container body 104 is generally transparent to facilitate viewing of the botanical specimen (when in the container body 104).

Figure 5:
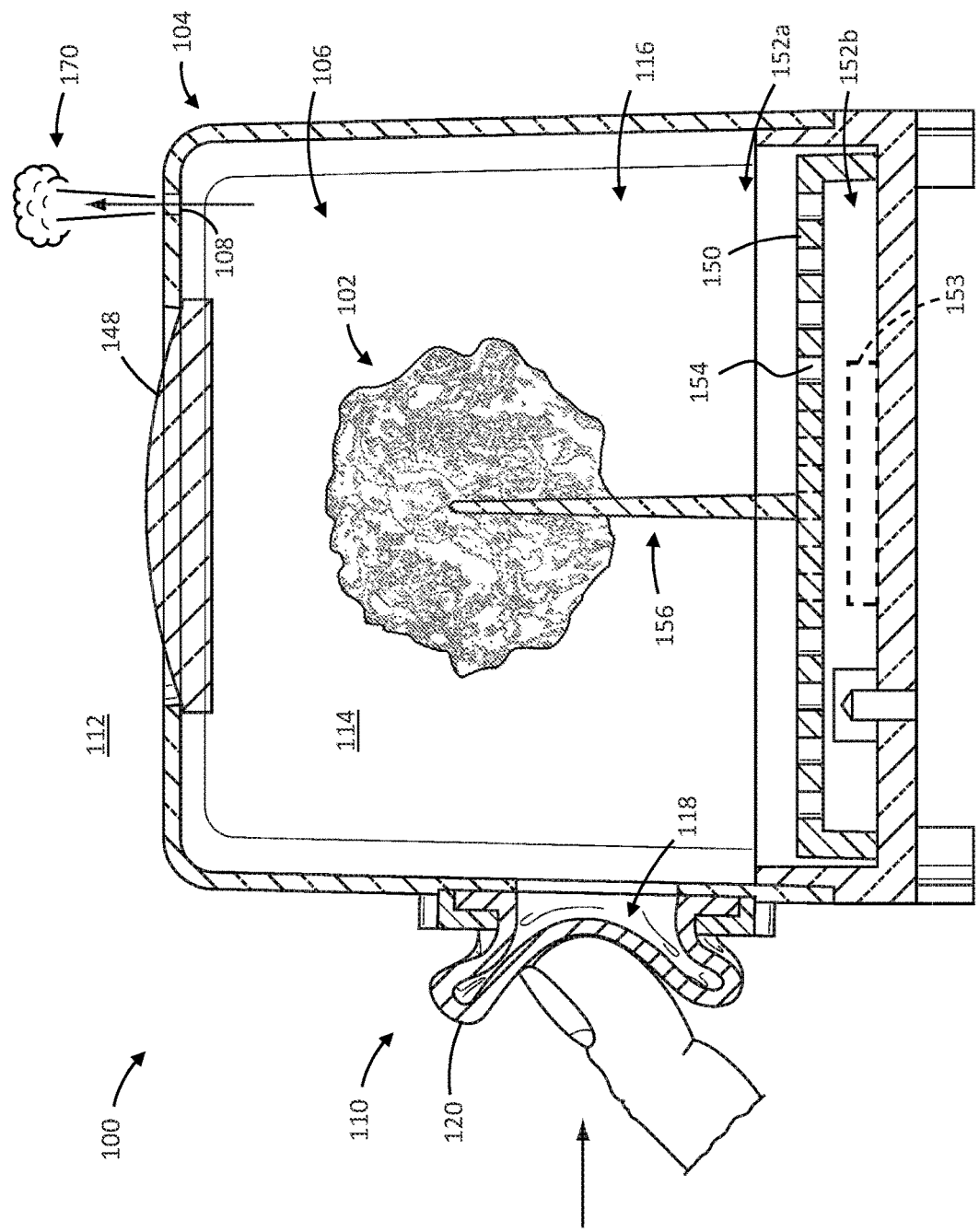
FIG. 5 is a cross-sectional view like that of FIG. 4, and showing a botanical specimen in the container and the pump in a contracted configuration.

Still referring to FIG. 1, in the example illustrated, the container 100 includes at least one scent discharge port 108 in the container body 104. The container 100 further includes an air pump 110 coupled to the container body 104. Referring to FIG. 5, in the example illustrated, the air pump 110 is operable to discharge the scented air 106 from within the container body 104 to environment 112 through the scent discharge port 108. In the example illustrated, the air pump 110 is hand-operable to discharge the scented air.

Figure 4:
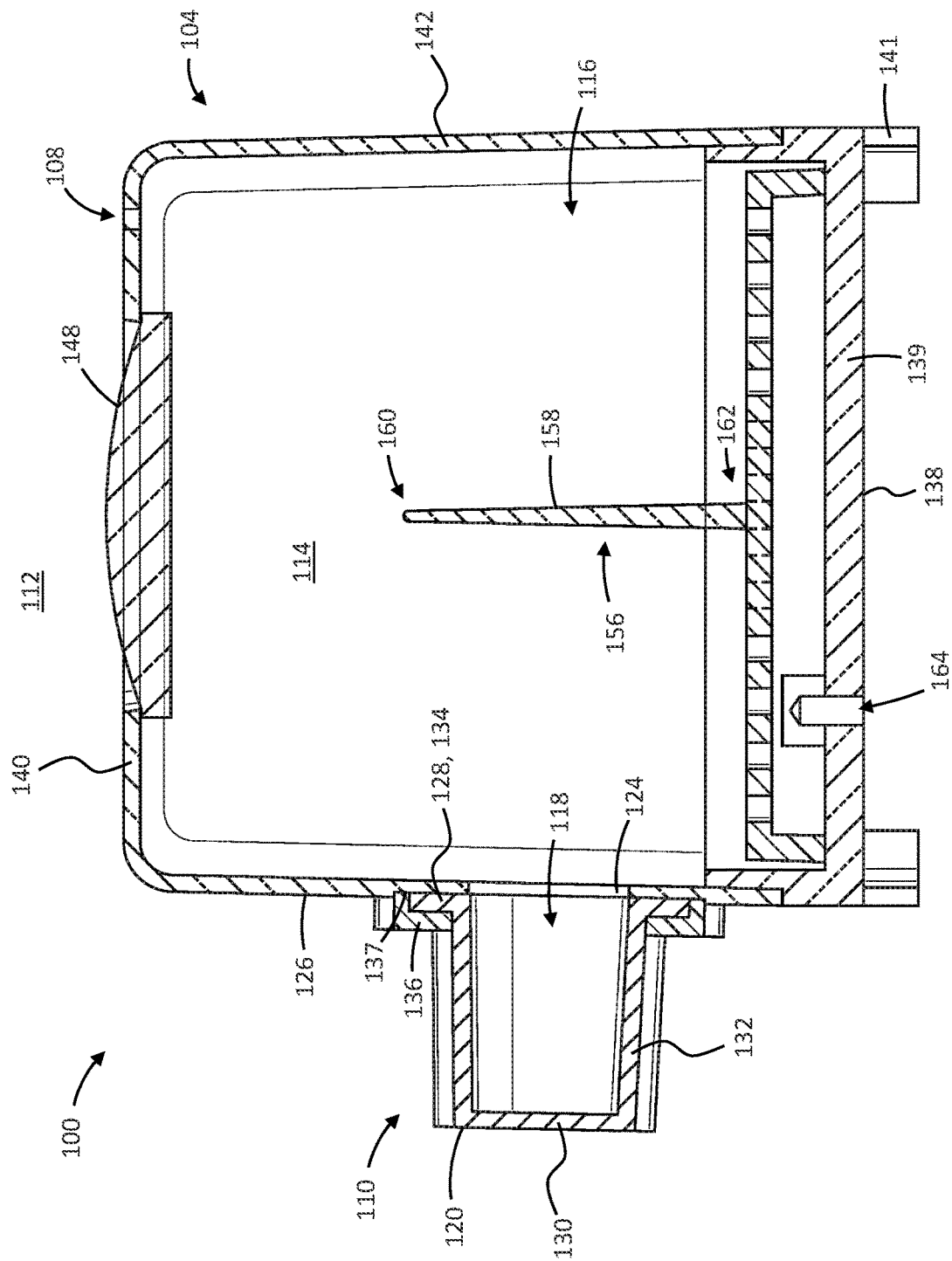
FIG. 4 is a cross-sectional view of the container of FIG. 1 taken along line 4-4 in FIG. 3, and showing an air pump of the container in an expanded configuration.

Referring to FIG. 4, in the example illustrated, the air pump 110 cooperates with the container body 104 to define an interior volume 114 of the display container 100. In the example illustrated, the interior volume 114 is in fluid communication with the scent discharge port 108. In the example illustrated, the interior volume 114 is kept at ambient pressure, and is open to the environment 112 through the scent discharge port 108. The interior volume 114 is otherwise generally sealed off from the environment 112. In the example illustrated, the interior volume 114 comprises an interior space 116 in the container body 104 for containing the botanical specimen 102 and the scented air 106 (FIG. 5).

Referring to FIGS. 4 and 5, in the example illustrated, the air pump 110 is movable between an expanded state (FIG. 4) and a contracted state (FIG. 5). Referring to FIG. 5, movement of the air pump 110 toward the contracted state reduces the interior volume 114 for discharging the scented air 106 from within the container body 104 (from the interior space 116, in the example illustrated) to the environment 112 through the scent discharge port 108. In the example illustrated, movement of the air pump 110 back toward the expanded state increases the interior volume 114 for drawing air into the interior volume 114 (into the interior space 116, in the example illustrated) from the environment 112. In the example illustrated, the air is drawn into the interior volume 114 through the scent discharge port 108.

Still referring to FIG. 5, in the example illustrated, the interior volume 114 comprises an air chamber 118 of the air pump 110, and movement of the air pump 110 to the contracted state collapses the air chamber 118 to reduce the interior volume 114. Movement of the air pump 110 to the expanded state expands the air chamber 118 to increase the interior volume 114.

Referring to FIG. 4, in the example illustrated, the air pump 110 comprises a resiliently deformable bulb 120 mounted to the container body 104. The bulb 120 has a bulb interior defining the air chamber 118. In the example illustrated, the bulb 120 is mounted over an aperture 124 in the container body 104, and the air chamber 118 is in fluid communication with the interior space 116 of the container body 104 via the aperture 124. In the example illustrated, the air pump 110 and the aperture 124 are spaced apart from the scent discharge port 108.

In the example illustrated, when the air pump 110 is in the expanded state, the bulb 120 projects outwardly from an exterior surface 126 of the container body 104 and is depressible inwardly toward the container body 104 from a resting position (FIG. 4) toward a depressed position (FIG. 5) to move the air pump 110 toward the contracted state and collapse the air chamber 118. In the example illustrated, the bulb 120 can be moved toward the depressed position by being pushed inwardly toward the container body 104 by an operator's hand. In the example illustrated, the aperture 124 is sized and shaped to limit depression of the bulb 120 for inhibiting the bulb 120 from being pushed substantially into the interior space 116.

Referring to FIG. 5, in the example illustrated, when in the depressed position and released, the bulb 120 is urged outwardly away from the container body 104 back toward the resting position to move the air pump 110 toward the expanded state and expand the air chamber 118. In the example illustrated, the bulb 120 is formed of an elastomeric material, and is of integral, unitary, one-piece construction. The elastomeric material has sufficient resiliency and is shaped to urge the bulb 120 back toward the resting position when the bulb 120 is depressed and released. The bulb 120 may be formed of, for example, silicone, rubber, synthetic rubber, neoprene, nitrile rubber (Buna-N), ethylene propylene diene monomer (EPDM), latex, nitrile, butyl, room-temperature-vulcanizing (RTV) silicone, or any other suitable material.

Referring to FIG. 4, in the example illustrated, the bulb 120 has a bulb base 128 mounted against the container body 104 about the aperture 124, a bulb endwall 130 opposite the bulb base 128 and spaced outwardly apart from the container body 104, and a bulb sidewall 132 extending between the bulb base 128 and the bulb endwall 130. The air chamber 118 (defined by the bulb interior) is bounded by the bulb endwall 130 and the bulb sidewall 132. The bulb endwall 130 is movable toward the container body 104 to move the bulb 120 toward the depressed position and collapse the air chamber 118. In some examples, the bulb sidewall 132 can be squeezed to move the air pump 110 to the contracted state and collapse the air chamber 118.

In the example illustrated, the bulb base 128 comprises a mounting flange 134 extending outwardly relative to an exterior of the bulb sidewall 132 and fixed against the container body 104. In the example illustrated, the mounting flange 134 is held between the container body 104 and a bulb retainer 136 fixed to the container body 104. In the example illustrated, the bulb retainer 136 circumscribes the exterior of the bulb sidewall 132 and extends over the mounting flange 134. In the example illustrated, the mounting flange 134 and a periphery of the bulb retainer 136 extending about the mounting flange 134 are disposed in a recessed step 137 in the exterior surface 126 of the container body 104, the step 137 circumscribing the aperture 124 (see FIG. 2).

In the example illustrated, when viewed normal to the bulb endwall 130, the bulb 120 is generally peanut shaped. The bulb 120 may have a different shape in other examples. For example, the bulb 120 may be cylindrical, hemispherical, cuboid, or have any other suitable shape.

Referring to FIG. 4, in the example illustrated, the container body 104 comprises a container base 138 for supporting the container 100 in an upright position, a container top wall 140 opposite the container base 138, and a container sidewall 142 extending between the container base 138 and the container top wall 140. In the example illustrated, the interior space 116 of the container body 104 is bounded by the container base 138, the container top wall 140, and the container sidewall 142. In the example illustrated, the container base 138 includes a base wall 139 and plurality of feet 141 extending downwardly from the base wall 139 for supporting the container 100 in the upright position.

In the example illustrated, the scent discharge port 108 is in the container top wall 140, and the air pump 110 is mounted to the container sidewall 142. In the example illustrated, the scent discharge port 108 extends through the container top wall 140 between the interior space 116 and the environment 112 and is open for providing fluid communication therebetween. In the example illustrated, each discharge port 108 is sized to generally inhibit any noticeable air flow between the interior volume 114 and environment 112 absent operation of the air pump 110. In the example illustrated, each port 108 is defined by a diameter 108a (FIG. 3) of less than ⅛ inch (3.2 mm). In some examples, the diameter 108a of each port 108 is between 1/32 inch (0.8 mm) and 3/32 inch (2.4 mm). In some examples, the diameter 108a of each port 108 is approximately 1/16 inch (1.6 mm). In the example illustrated, the container 100 includes two spaced apart discharge ports 108 in the container top wall 140.

In the example illustrated, the container top wall 140 and the container sidewall 142 are generally transparent to facilitate viewing of the botanical specimen 102. In the example illustrated, the container base 138 is also generally transparent.

Figure 2:
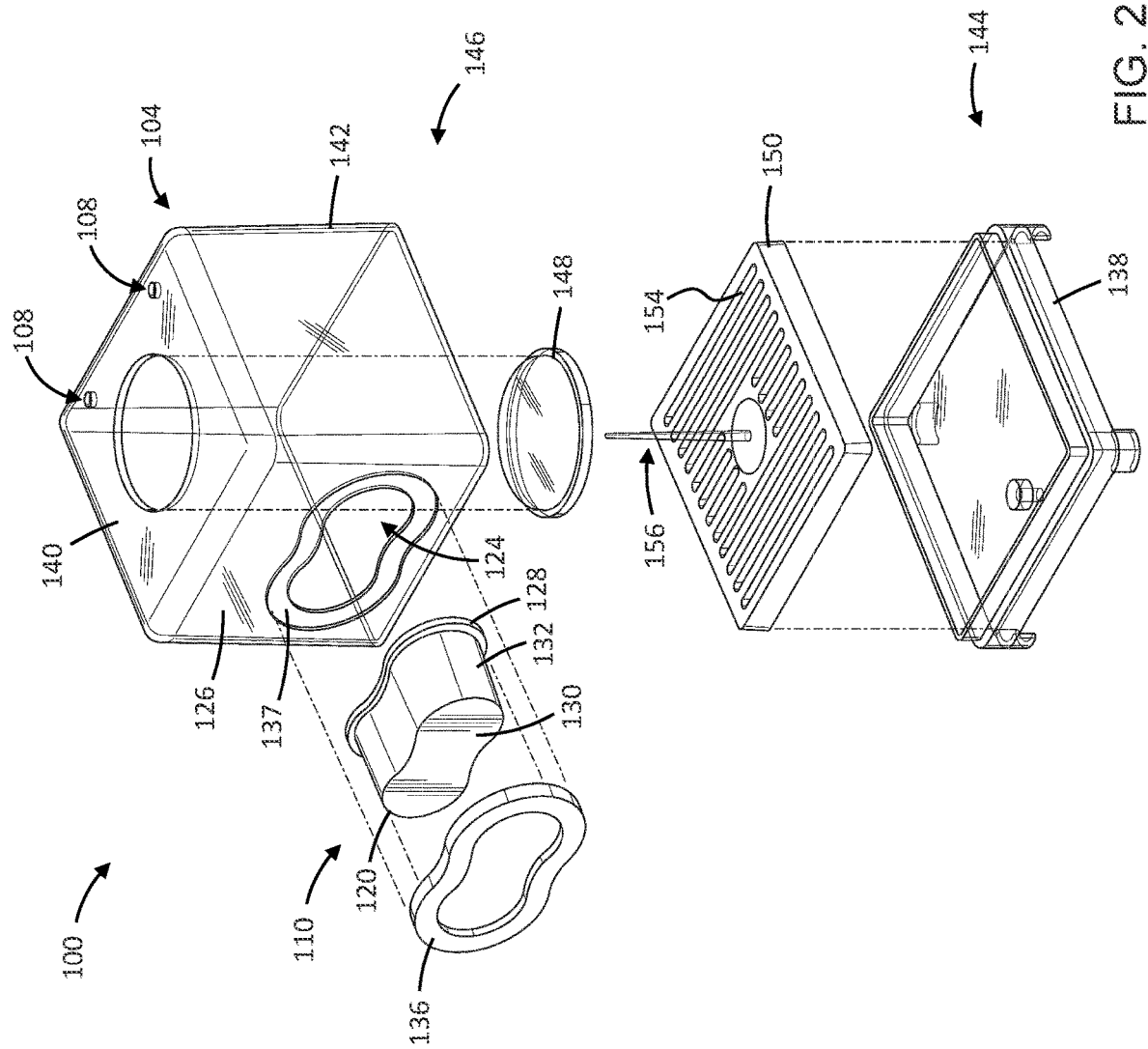
FIG. 2 is an exploded view of the container of FIG. 1.

Referring to FIG. 2, in the example illustrated, the container body 104 has a container first portion 144 (also referred to as a lower portion 144 with respect to the illustrated example) comprising the container base 138 and a container second portion 146 (also referred to as an upper portion 146 with respect to the illustrated example) comprising the container top wall 140. The upper portion 146 is secured to the lower portion 144 of the container body 104 during use of the container 100. The upper portion 146 may be secured to the lower portion 144 through, for example, friction fit, locking tabs, a locking ring, screws, adhesive tape, or any other suitable manner. The upper portion 146 can be detachable from the lower portion 144 to facilitate insertion of the botanical specimen 102 into the display container 100 and removal of the botanical specimen from within the display container 100. In the example illustrated, the upper portion 146 further comprises the container sidewall 142.

In the example illustrated, the container body 104 is generally rigid, and can be formed of, for example, a transparent polymeric material. The container body 104 may be formed of, for example, acrylic, polycarbonate, polyvinyl chloride (PVC), acrylonitrile butadiene styrene (ABS), polyethylene terephthalate glycol (PETG), polyethylene terephthalate (PET), or any other suitable material.

Figure 3:
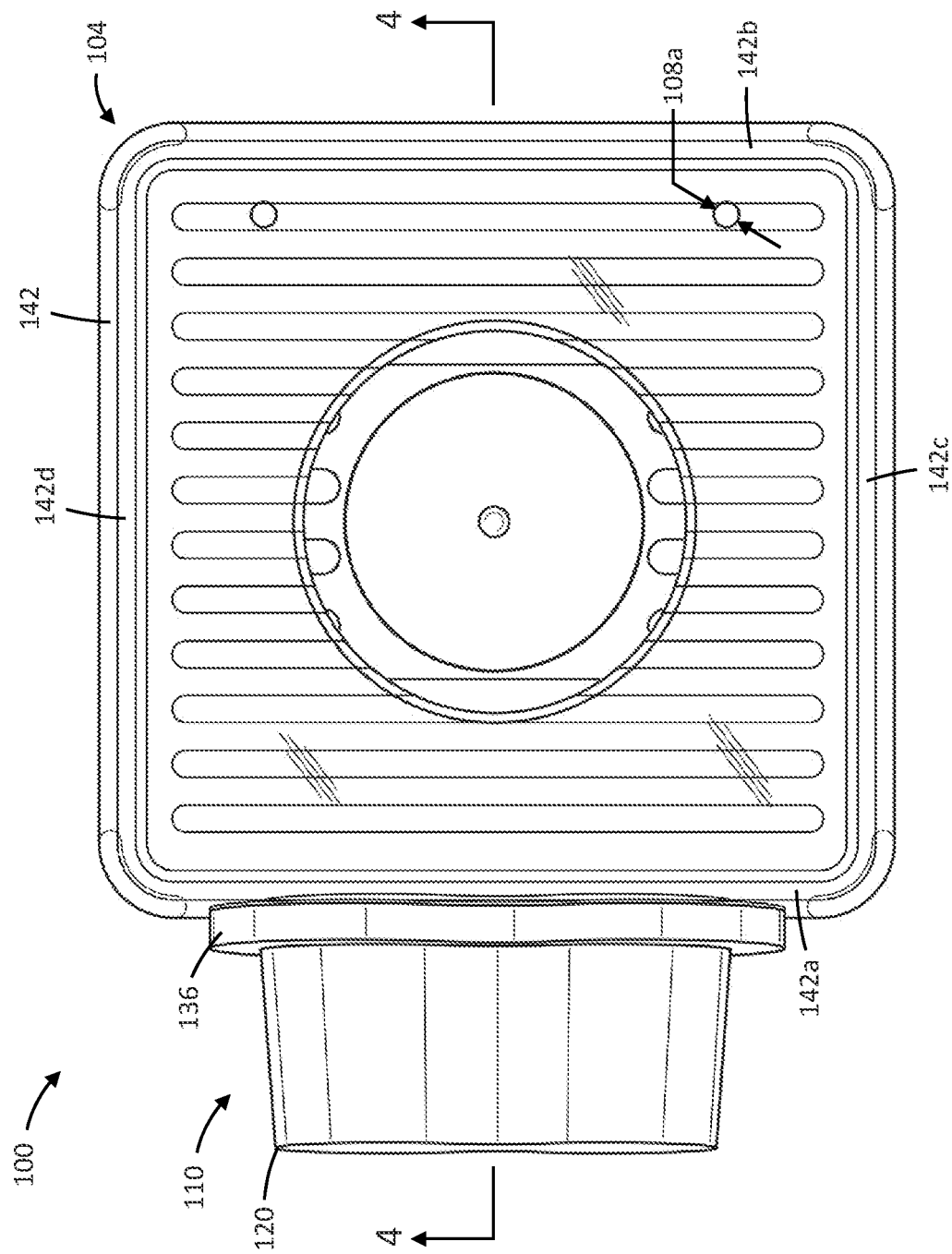
FIG. 3 is a top view of the container of FIG. 1.

In the example illustrated, the container body 104 has a generally cubic shape. Referring to FIG. 3, in the example illustrated, the container sidewall 142 comprises a sidewall first portion 142a, a sidewall second portion 142b horizontally opposite the sidewall first portion 142a, a sidewall third portion 142c extending between the sidewall first portion 142a and the sidewall second portion 142b, and a sidewall fourth portion 142d horizontally opposite the sidewall third portion 142c and extending between the sidewall first portion 142a and the sidewall second portion 142b. In the example illustrated, each of the sidewall portions 142a-d is generally planar. The container body 104 may have a different shape in other examples.

Referring to FIG. 5, in the example illustrated, the container body 104 includes a viewing lens 148 for viewing of the botanical specimen 102. The viewing lens 148 can comprise, for example, a magnification lens for providing a magnified view of the botanical specimen 102. In the example illustrated, the viewing lens 148 forms part of the container top wall 140 of the container body 104.

In the example illustrated, the display container 100 further includes a platform 150 in the container body 104. In the example illustrated, the platform 150 serves as a vented partition separating the interior space 116 into a first compartment (also referred to as an upper compartment 152a with respect to the illustrated example) for containing the botanical specimen 102 and a second compartment (also referred to as a lower compartment 152b with respect to the illustrated example) for containing a humidity control package 153 (shown schematically in dashed lines in FIG. 5). The platform 150 has a plurality of vents 154 for providing fluid communication between the upper and lower compartments 152a, 152b to facilitate regulation of humidity in the interior space 116. In the example illustrated, the platform 150 is supported on the container base 138 of the container body 104.

In other examples, the display container can include a vented partition oriented generally vertically to separate the interior space into horizontally spaced apart compartments (e.g. a front compartment for containing the botanical sample and a rear compartment for containing the humidity control package).

Referring to FIG. 5, in the example illustrated, the container 100 further includes a specimen retainer 156 in the interior space 116 of container body 104 for retaining the botanical specimen 102 at a predetermined location in the interior space 116. Referring to FIG. 4, in the example illustrated, the specimen retainer 156 comprises a mounting spike 158 for impaling the botanical specimen 102. In the example illustrated, the mounting spike 158 is supported on and projects upwardly from the platform 150. In the example illustrated, the mounting spike 158 has a spike base 160 fixed to the platform 150, and a tip 162 spaced vertically above the spike base 160 and on which the botanical specimen 102 is impaleable. In some examples, the platform 150 may be omitted, and the mounting spike 158 may be, for example, formed integrally with or mounted on the container base 138.

Still referring to FIG. 4, in the example illustrated, the container body 104 includes an anchoring feature 164 in the container base 138 to facilitate attachment of a security tether. In the example illustrated, the anchoring feature 164 comprises a recess open to a bottom of the base wall 139 (e.g. for receiving a fastener in threaded engagement to secure the security tether to the container base).

Figure 6:
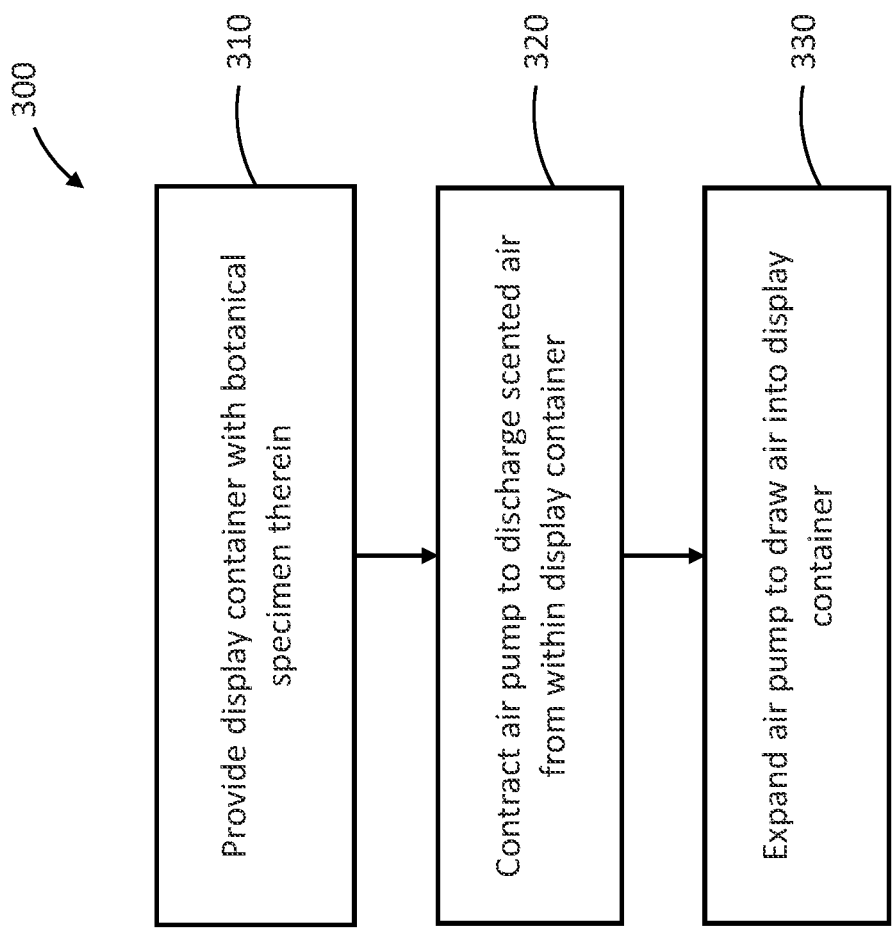
FIG. 6 is a flow chart showing an example process for sampling an aroma of a botanical specimen contained within a display container like the container of FIG. 1.

Referring to FIG. 6, an example process 300 for sampling an aroma of a botanical specimen using a display container similar to the container 100 is shown, and will be described with respect to the container 100 and botanical specimen 102.

Referring to FIGS. 5 and 6, at step 310 of the process 300, the display container 100 is provided with the botanical specimen 102 contained therein.

At step 320, the air pump 110 is contracted to discharge the scented air 106 from within the container 100 to the environment 112 through the scent discharge port 108. In the example illustrated, step 320 includes reducing the interior volume 114 of the display container 100, which increases air pressure in the interior volume 114 to urge discharge of the scented air through the port 108 in a puff 170 of scented air (FIG. 5). In the example illustrated, step 320 includes collapsing the air chamber 118 to reduce the interior volume 114. In the example illustrated, step 320 includes depressing the bulb 120 to collapse the air chamber 118 (e.g. by pushing the bulb inwardly toward the container body 104 from the resting position to the depressed position).

The process 300 can optionally include, at step 330, expanding the air pump 110 to draw air into the display container 100 from the environment 112. In the example illustrated, the air is drawn into the display container 100 through the scent discharge port 108. In the example illustrated, step 330 includes increasing the interior volume 114 of the display container 100, which can reduce air pressure in the interior volume 114 to suction air into the container 100 from the environment 112 through the port 108. In the example illustrated, step 330 comprises expanding the air chamber 118 to increase the interior volume 114. In the example illustrated, step 330 comprises releasing the bulb 120 to expand the air chamber 118 (e.g. to permit the bulb to expand back to its resting position). Steps 320 and 330 can optionally be repeated to discharge the scented air 106 in successive puffs 170.

Figure 7:
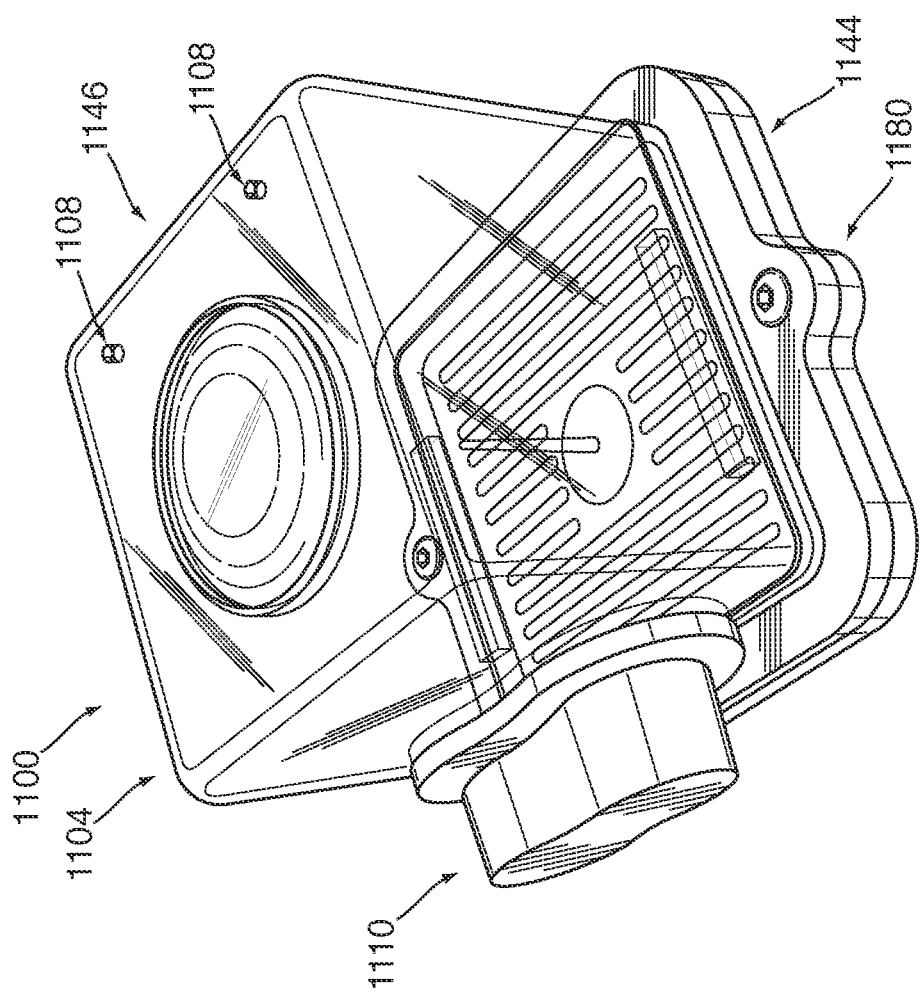
FIG. 7 is a perspective view of another example display container.

Referring to FIG. 7, another example display container 1100 for displaying an aromatic botanical specimen is illustrated. The display container 1100 has similarities to the display container 100, and like features are identified using like references characters, incremented by 1000.

Figure 8:
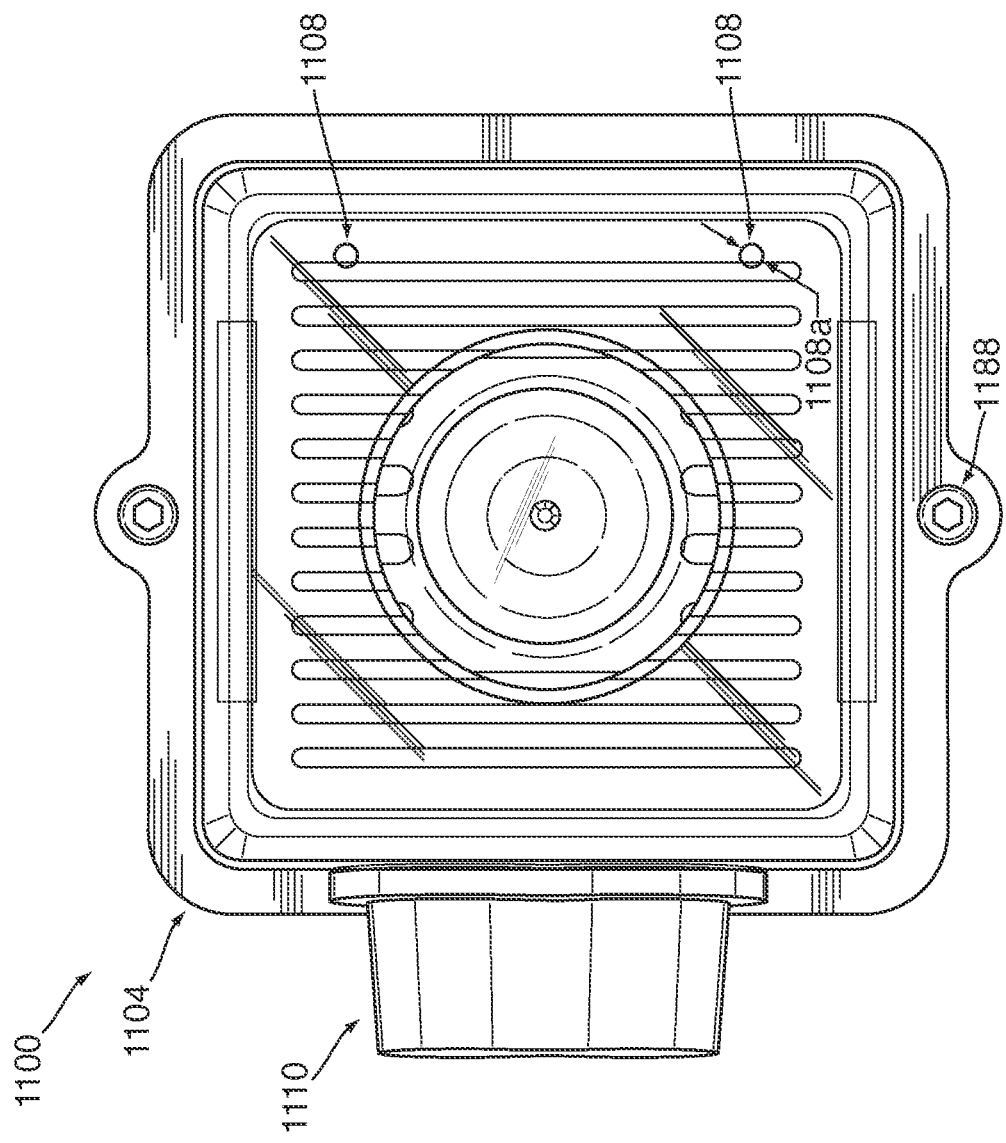
FIG. 8 is a top view of the display container of FIG. 7.

In the example illustrated, the display container 1100 includes a container body 1104 for enclosing the botanical specimen and scented air having a scent of the botanical specimen, at least one scent discharge port 1108 in the container body 1104, and an air pump 1110 coupled to the container body 1104 and operable to discharge the scented air from within the container body 1104 to environment through the scent discharge port 1108. Referring to FIG. 8, in the example illustrated, the display container 1100 includes a plurality of scent discharge ports 1108. In the example illustrated, each scent discharge port 1108 has a diameter 1108a of approximately 1/16 inch (1.6 mm).

Referring to FIG. 7, in the example illustrated, the container body 1104 has a container first portion 1144 and a container second portion 1146 detachably secured to the container first portion 1144. When detachably secured, the container first and second portions 1144, 1146 cooperate to generally enclose an interior space for containing the botanical specimen and scented air. In the example illustrated, the container first portion 1144 comprises a container base for supporting the container 1100 in an upright position, and the container second portion 1146 comprises a container top wall and a container sidewall extending downwardly from a periphery of the container top wall toward the container base (and enclosing the container interior horizontally).

Figure 9:
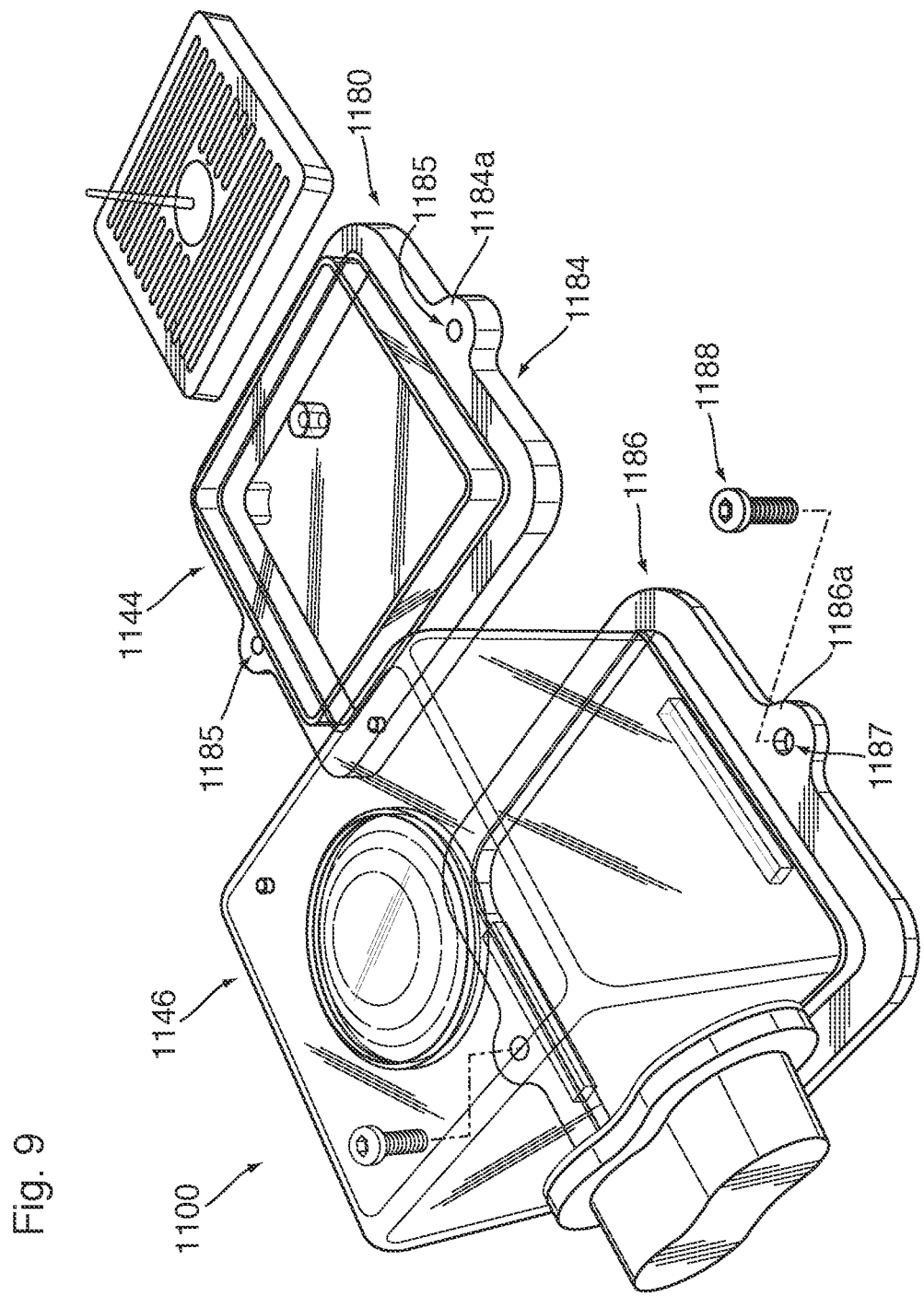
FIG. 9 is a partially exploded perspective view of the display container of FIG. 7.

In the example illustrated, the display container 1100 includes a lock 1180 for detachably locking the container second portion 1146 to the container first portion 1144. Referring to FIG. 9, in the example illustrated, the lock 1180 includes a lock first portion 1184 fixed relative to the container first portion 1144 (through an adhesive or integral formation, for example) and a lock second portion 1186 fixed relative to the container second portion 1146 (through an adhesive or integral formation, for example). In the example illustrated, the lock first portion 1144 is securable to the lock second portion 1186 through one or more removable fasteners 1188 (e.g. screws) to detachably lock the container second portion 1146 to the container first portion 1144, which can help inhibit tampering and/or unauthorized opening of the display container 1100. The fasteners 1188 can be removed to detach the second portion 1146 of the container 1100 from the first portion 1144 for opening the display container 1100 to, for example, insert or remove the botanical specimen from the interior and/or for maintenance of the container 1100.

In the example illustrated, the lock 1180 comprises a locking ring, with the lock first portion 1184 having a flange first portion 1184a extending about the container first portion 1144 and the lock second portion 1186 having a flange second portion 1186a extending about the container second portion 1146 adjacent its lower periphery for engagement with the flange first portion 1184a. In the example illustrated, the flange first portion 1184a has a pair of first holes 1185 passing vertically therethrough on horizontally opposite sides of the container body 1104, and the flange second portion 1186a has a pair of second holes 1187 passing vertically therethrough for registration with the pair of first holes 1186 to receive the fasteners 1188. In the example illustrated, the pair of first holes 1185 are threaded and the pair of second holes 1187 have a clearance fit to facilitate insertion of the fasteners 1188 (in the form of screws, in the example illustrated) from above through the second holes 1187 and into threaded engagement with the first holes 1185 to bring the flange second portion 1186a into engagement with the flange first portion 1184a and lock the container second portion 1146 to the container first portion 1144.

The invention claimed is:

1. An insert for a display container, comprising:
   a) a vented partition positionable in an interior of the display container to separate the interior into a first compartment for containing a botanical specimen viewable through the display container and a second compartment in fluid communication with the first compartment through the vented partition; and
   b) a specimen retainer coupled to and projecting from the vented partition into the first compartment for retaining the botanical specimen thereon.

2. The insert of claim 1, wherein the specimen retainer extends between a base adjacent and fixed to the vented partition and a tip spaced apart from the partition for impaling the botanical specimen.

3. The insert of claim 2, wherein the specimen retainer is tapered toward the tip.

4. The insert of claim 1, wherein the specimen retainer comprises an elongate protrusion.

5. The insert of claim 1, wherein the specimen retainer comprises a mounting spike for impaling the botanical specimen.

6. The insert of claim 1, wherein the vented partition comprises a partition wall positionable across the interior for separating the interior into the first and second compartments, and a plurality of vent apertures extending through the partition wall for providing fluid communication between the first and second compartments.

7. The insert of claim 6, wherein the vent apertures are elongate and extend parallel with and are spaced apart from each other.

8. The insert of claim 6, wherein the vented partition includes a sidewall extending from a periphery of the partition wall along the second compartment.

9. The insert of claim 1, wherein the vented partition is generally opaque.

10. The insert of claim 1, wherein the vented partition is positionable in the interior in a generally horizontal orientation to vertically separate the first compartment and the second compartment, with the specimen retainer projecting upwardly from the vented partition.

11. The insert of claim 1, wherein the vented partition is positionable in the interior in a generally vertical orientation to horizontally separate the first compartment and the second compartment.

12. A kit for display of botanical specimens, including:
   a) an insert for a display container, including:
      i) a vented partition positionable in an interior of the display container to separate the interior into a first compartment for containing a botanical specimen viewable through the display container and a second compartment in fluid communication with the first compartment through the vented partition; and
      ii) a specimen retainer coupled to and projecting from the vented partition into the first compartment for retaining the botanical specimen thereon; and
   b) a humidity control package positionable in the second compartment for regulating humidity in the interior.

13. The kit of claim 12, wherein the specimen retainer comprises a mounting spike for impaling the botanical specimen.

14. The kit of claim 12, wherein the vented partition comprises a partition wall positionable across the interior for separating the interior into the first and second compartments, and a plurality of vent apertures extending through the wall for providing fluid communication between the first and second compartments.

15. The kit of claim 12, further comprising the display container.

16. The kit of claim 15, wherein the vented partition is positionable in the interior in a generally horizontal orientation to vertically separate the first compartment and the second compartment, the first compartment defining an upper compartment above the partition and the second compartment defining a lower compartment below the partition, and the specimen retainer projecting upwardly from the vented partition into the first compartment.

17. The kit of claim 15, wherein the vented partition is positionable in the interior in a generally vertical orientation to horizontally separate the first compartment and the second compartment, the first compartment defining a front compartment of the display container and the second compartment defining a rear compartment of the display container.

18. The kit of claim 15, wherein the container has a generally cubic shape and the vented partition is generally rectangular.

19. The kit of claim 15, wherein the display container has one or more scent ports extending therethrough for sampling an aroma of the botanical specimen.

20. The kit of claim 15, wherein the display container has an integrated lens for viewing of the botanical sample.

* * * * *